United States Patent
Srinivasan et al.

(10) Patent No.: US 10,571,374 B2
(45) Date of Patent: Feb. 25, 2020

(54) METHOD AND DEVICE TO EXTRACT AN ANALYTE FROM A SAMPLE WITH GAS ASSISTANCE

(71) Applicant: DIONEX CORPORATION, Sunnyvale, CA (US)

(72) Inventors: Kannan Srinivasan, Tracy, CA (US); SM Rahmat Ullah, Fremont, CA (US)

(73) Assignee: Dionex Corporation, Sunnyvale, CA (US)

( * ) Notice: Subject to any disclaimer, the term of this patent is extended or adjusted under 35 U.S.C. 154(b) by 303 days.

(21) Appl. No.: 15/232,897

(22) Filed: Aug. 10, 2016

(65) Prior Publication Data

US 2016/0349158 A1    Dec. 1, 2016

Related U.S. Application Data

(63) Continuation of application No. 13/599,837, filed on Aug. 30, 2012, now Pat. No. 9,440,166.

(51) Int. Cl.
*G01N 1/00* (2006.01)
*G01N 1/40* (2006.01)
(Continued)

(52) U.S. Cl.
CPC ....... *G01N 1/4055* (2013.01); *B01D 11/0203* (2013.01); *B01D 11/0219* (2013.01); *B01D 11/0292* (2013.01); *G01N 1/04* (2013.01)

(58) Field of Classification Search
CPC .................................................. G01N 1/4055
(Continued)

(56) References Cited

U.S. PATENT DOCUMENTS 3,117,084 A    1/1964  Nick et al.
4,246,291 A    1/1981  Prasad et al.
(Continued)

FOREIGN PATENT DOCUMENTS

CN    201632088 U    11/2010
CN    202136830 U    2/2012
(Continued)

OTHER PUBLICATIONS

Vollmer et al. "Agilent 1260 Infinity Hybrid SFC/UHPLC System" Agilent Technologies, Inc., 2012 Published in the USA, Feb. 1, 2012 5990-9514EN (Year: 2012).*

(Continued)

*Primary Examiner* — Christine T Mui
*Assistant Examiner* — Emily R. Berkeley
(74) *Attorney, Agent, or Firm* — Timothy J. Ohara

(57) ABSTRACT

A method of extracting an analyte from a sample is described. The sample is added to a sample container. A liquid solvent and a gas are added into the sample container. The addition of the gas is controlled to establish an elevated pressure within the sample container. The liquid solvent is heated to an elevated temperature that is below the boiling temperature of the liquid solvent at the elevated pressure. A type of gas is used that does not transition to a supercritical fluid at the elevated temperature and pressure used in the extraction process. The analyte can dissolve from the solid sample into the liquid solvent. Next, at least a portion of the liquid solvent containing the dissolved analyte can be removed from the sample container for subsequent analysis.

7 Claims, 4 Drawing Sheets

(51) Int. Cl.
*B01D 11/02* (2006.01)
*G01N 1/04* (2006.01)

(58) Field of Classification Search
USPC .......................................................... 436/178
See application file for complete search history.

(56) References Cited

U.S. PATENT DOCUMENTS

| | | | |
|---|---|---|---|
| 4,276,315 | A | 6/1981 | Katz et al. |
| 4,546,088 | A | 10/1985 | Karlberg et al. |
| 4,832,577 | A | 5/1989 | Avramidis |
| 4,840,730 | A | 6/1989 | Saxena |
| 5,147,538 | A | 9/1992 | Wright et al. |
| 5,338,575 | A | 8/1994 | Ben-Nasr et al. |
| 5,372,716 | A * | 12/1994 | Levy et al. ............... 210/198.2 |
| 5,660,727 | A | 8/1997 | Gleave et al. |
| 5,716,525 | A | 2/1998 | Nickerson |
| 5,728,851 | A | 3/1998 | Franke |
| 5,785,856 | A | 7/1998 | Gleave et al. |
| 5,843,311 | A | 12/1998 | Richter et al. |
| 6,425,284 | B1 | 7/2002 | Srinivasan et al. |
| 6,544,484 | B1 | 4/2003 | Kaufman et al. |
| 6,568,245 | B2 | 5/2003 | Kaufman |
| 6,648,609 | B2 | 11/2003 | Berger et al. |
| 7,008,528 | B2 * | 3/2006 | Mitchell et al. ............. 208/390 |
| 7,964,224 | B2 | 6/2011 | Beavers |
| 7,964,411 | B2 | 6/2011 | Dasgupta et al. |
| 2005/0266130 | A1 | 12/2005 | Aoki |
| 2009/0218238 | A1 | 9/2009 | Dasgupta et al. |
| 2009/0221079 | A1 | 9/2009 | Srinivasan et al. |
| 2012/0028368 | A1 | 2/2012 | Srinivasan et al. |
| 2012/0070360 | A1 | 3/2012 | Wissemborski et al. |

FOREIGN PATENT DOCUMENTS

| | | |
|---|---|---|
| GB | 273307 | 6/1927 |
| WO | WO9534360 A1 | 12/1995 |
| WO | 2008099131 A1 | 8/2008 |

OTHER PUBLICATIONS

"Vapor Pressure Graph" accessed by examiner at http://encyclopedia.airliquide.com/images_encyclopedia/VaporPressureGraph/Propane_Vapor_Pressure.GIF on Mar. 20, 2014.*

"Air Liquide: Gas Encyclopedia" accessed by the examiner at http://encyclopedia.airliquide.com/encyclopedia.asp?LanguageID=11&CountryID=19&Formula=&GasID=53&UNNumber= on Mar. 20, 2014.*

Bowadt et al., Supercritical Fluid Extraction in Environmental Analysis, J of Chromatrography A, 703, pp. 549-571, 1995.

Harvey et al., Comprehensive Review of Applicable Supercritical Fluid Extraction Research. PNNL-13643, Pacific Northwest National Laboratory, Richland, WA, 2001.

Kumar et al., High Hydrostatic Pressure Extraction of Antioxidants from Morinda Citrifolia Fruit—Process Parameters Optimization, J of Engineering Science and Technology, vol. 1, No. 1, pp. 41-49, 2006.

Lang et al., Supercritical Fluid Extraction in Herbal and Natural Product Studies—a Practical Review, Talanta, 52, pp. 771-782, 2001.

Product Manual for ASE Prep CR H+ form (Thermo Scientific Dionex), 2009.

Sunarso et al., Journal of Hazardous Materials, 161, pp. 1-20, 2009.

Technology Watch, vol. 2, Issue 1, pp. 1-12, Jul. 2005.

"Air Liquide: Gas Encyclopedia" accessed by the examiner athttp://encyclopedia.airliquide.com/encyclopedia.asp?LanguageID=11&CountryiD=19&Formula&GasI D=53&UNNumber— on Mar. 20, 2014.

"Vapor Pressure Graph" accessed by examiner at http://encyclopedia.airliquide.com/images.sub.—encyclopedie/VaporPressur—eGraph/Propane.sub.—Vapor.sub.—Pressure.GIF on Mar. 20, 2014.

* cited by examiner

METHOD AND DEVICE TO EXTRACT AN ANALYTE FROM A SAMPLE WITH GAS ASSISTANCE

CROSS-REFERENCE TO RELATED APPLICATION

This application is a continuation under 35 U.S.C. § 120 and claims the priority benefit of pending patent application Ser. No. 13/599,837, filed Aug. 30, 2012, entitled "Method and Device to Extract an Analyte from a Sample with Gas Assistance," and is incorporated by reference in its entirety.

BACKGROUND

In an effort to make the world a healthier, cleaner, and safer place, there is interest in analyzing for chemicals of interest as it relates to industrial processes. For example, processed food items such as infant baby formula powder can be analyzed for lipid content or soil samples can be analyzed for toxic levels of a pesticide. These applications have created a need to analyze a large number of solid samples in an automated manner with a fast turn-around time.

In many instances, the chemical of interest must first be extracted from a solid sample so that it can be measured with an analytical technique. Solid liquid extraction is a method to solubilize an analyte from a solid sample. A solid sample can be any material or matrix that contains an analyte of interest. An analyte is a chemical that can be separated from a solid sample and subsequently quantitated using an analytical technique. Examples of an analyte may be an active ingredient in a drug tablet, a pesticide in a soil sample, or a lipid in a food item such as infant baby formula or corn chips.

In solid liquid extraction, the solid sample is treated with a liquid solvent to dissolve the analyte. A liquid solvent is selected that can solubilize the analyte, but not necessarily all of the other materials in the solid sample. Once the liquid solvent contains the dissolved analyte, it can be removed from any undissolved portion of the solid sample and then quantitated using a suitable analytical technique. An example of an analytical technique may be a liquid chromatograph coupled with a detector such as a conductivity detector, a charge detector, a UV-VIS spectrometer, or a mass-spectrometer.

In order to accelerate the solid liquid extraction process, the liquid solvent may be heated to enhance the solubility of the analyte. However, the temperature cannot be too high because the analyte can decompose or react with other chemicals in the solid sample. In addition, high temperature can cause the liquid solvent to vaporize and attenuate the solvating capability.

A supercritical fluid can be used to accelerate the solid liquid extraction process. A supercritical fluid is a substance at a temperature and a pressure above its critical point, and thus, develops properties similar to a liquid. An example of a supercritical fluid is carbon dioxide that is at a temperature and a pressure above 31.1° C. and 1070 pounds per square inch (PSI), respectively. While supercritical carbon dioxide is a good solvent for some applications that have low to moderate polarity analytes, it is less effective for extractions of high molecular weight and polar analytes. For example, environmental pollutants such as chlorinated dioxins from fly ash, polycyclic aromatic hydrocarbons, pesticides, semi volatile organic carbons, and nitroaromatics from urban air particulate matter have been reported (Harvey S, C W Wright, and B W Wright. 2001. Comprehensive Review of Applicable Supercritical Fluid Extraction Research. PNNL-13643, Pacific Northwest National Laboratory, Richland, W A; J. Chromatogr. A 703 (1995) 549-5; Journal of Hazardous Materials 161 (2009) 1-20; and U.S. Pat. No. 5,147,538, which are hereby fully incorporated by reference herein). For sample modifiers such as methanol or ethanol, usually in the <20 mole percent range, can be added to increase the polarity and have worked to some degree (Technology Watch, Volume 2, Issue 1, pp 1-12, July 2005; and Talanta 53 (2001) 771-782, which are hereby fully incorporated by reference herein). These modifiers do not work for all matrices, and thus, Applicants believe that there is a need for a method that allows extraction of species from a variety of matrices. It should be noted supercritical fluid liquid extraction requires relatively high pressures (typically much greater than about 100 PSI) making the instrumentation relatively expensive.

In solid liquid extraction, Applicants believe that there is a need to have a more efficient extraction process with a reduced amount of liquid solvent because proper clean-up and disposal of used liquid solvent can be expensive. At the same time, Applicants believe that this extraction process should be fast and use relatively inexpensive instrumentation that is amenable to automation.

SUMMARY

A method of extracting an analyte from a sample is described. The sample is added to a sample container. A mixture of a liquid solvent and a gas is added into the sample container. The addition of the gas is controlled to establish a superatmospheric pressure P within the sample container. The liquid solvent is heated to an elevated temperature T, where T is below the boiling temperature of the liquid solvent at the superatmospheric pressure P. In addition, either the pressure P or the temperature T is maintained below the critical point of the gas. The analyte dissolves from the solid sample into the liquid solvent. Next, at least a portion of the liquid solvent can be removed from the sample container and subsequently analyzed.

A method of extracting an analyte from a sample is described that uses an alternating segmented flow of a gas and then a liquid solvent. The sample is added to a sample container. A liquid solvent is added into the sample container over a first time period. Next, a gas is added over a second time period to establish a superatmospheric pressure P within the sample container. A ratio of the first time period divided by the second time period includes a value less than about 15. The liquid solvent is heated to an elevated temperature T, where T is below the boiling temperature of the liquid solvent at the superatmospheric pressure P. In addition, either the pressure P or the temperature T is maintained below the critical point of the gas. The analyte dissolves from the solid sample into the liquid solvent. At least a portion of the liquid solvent can be removed from the sample container and subsequently analyzed.

An apparatus configured to extract an analyte from a first sample is described. The apparatus includes a compressed gas source, a liquid solvent pump, a fluid junction, a first sample container, and a heating source. The compressed gas source can be configured to supply a gas at a superatmospheric pressure. The liquid solvent pump can be configured to transport a liquid solvent. The fluid junction can include a first inlet, a second inlet, and an outlet. The first inlet and second inlet are both fluidically connected to the outlet. The first inlet can also be in fluidic communication with the compressed gas source. The second inlet can also be in fluidic communication with the liquid solvent pump. The outlet can also be configured to flow a mixture of the gas and the liquid solvent at the same time. The first sample container can be configured to contain the first sample. An inlet of the first sample container can be fluidically connected to the outlet of the fluid junction. The first sample container can also be configured to allow the gas and the liquid solvent to flow from an inlet to an outlet of the first sample container. The heating source can be configured to heat the liquid solvent. In another aspect, the apparatus may be configured to extract more than one sample at the same time. A second sample container can be configured to contain a second sample and also be fluidically connected to the outlet of the fluid junction. The second sample container can also be configured to allow the gas and the liquid solvent to flow from an inlet to an outlet of the second sample container, and in which a flow of the liquid solvent is about evenly split between the first and second sample containers.

An apparatus configured to extract an analyte from a sample is described that uses an alternating segmented flow of a gas and then a liquid solvent. The apparatus includes a compressed gas source, a liquid solvent pump, a valve, a microprocessor, a sample container, and a heating source. The compressed gas source can be configured to supply a gas at a superatmospheric pressure. The liquid solvent pump can be configured to transport a liquid solvent. The valve can include a first position and a second position where the first position directs the liquid solvent from the liquid solvent pump into the sample container, and the second position directs the gas from the compressed gas source into the sample container to establish a superatmospheric pressure P within the sample container. The valve is coupled to a microprocessor. The microprocessor is configured to alternate the valve between the first position over a first time period and the second position over a second time period where a ratio of the first time period divided by the second time period comprises a value less than about 15. The sample container can be configured to contain the sample. The heating source can be configured to heat the liquid solvent.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements). A detailed understanding of the features and advantages of the present invention will be obtained by reference to the following detailed description that sets forth illustrative embodiments, in which the principles of the invention are utilized, and the accompanying drawings of which.

DETAILED DESCRIPTION OF EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

A solid liquid extraction apparatus will be described that is configured to have gas assistance. Such an apparatus will allow an analyte to be extracted from a solid sample with a liquid solvent in an efficient manner. The solid liquid extraction apparatus provides a gas to increase the pressure of the sample container and also a heater to increase the temperature of the liquid solvent at the same time.

Figure 1:
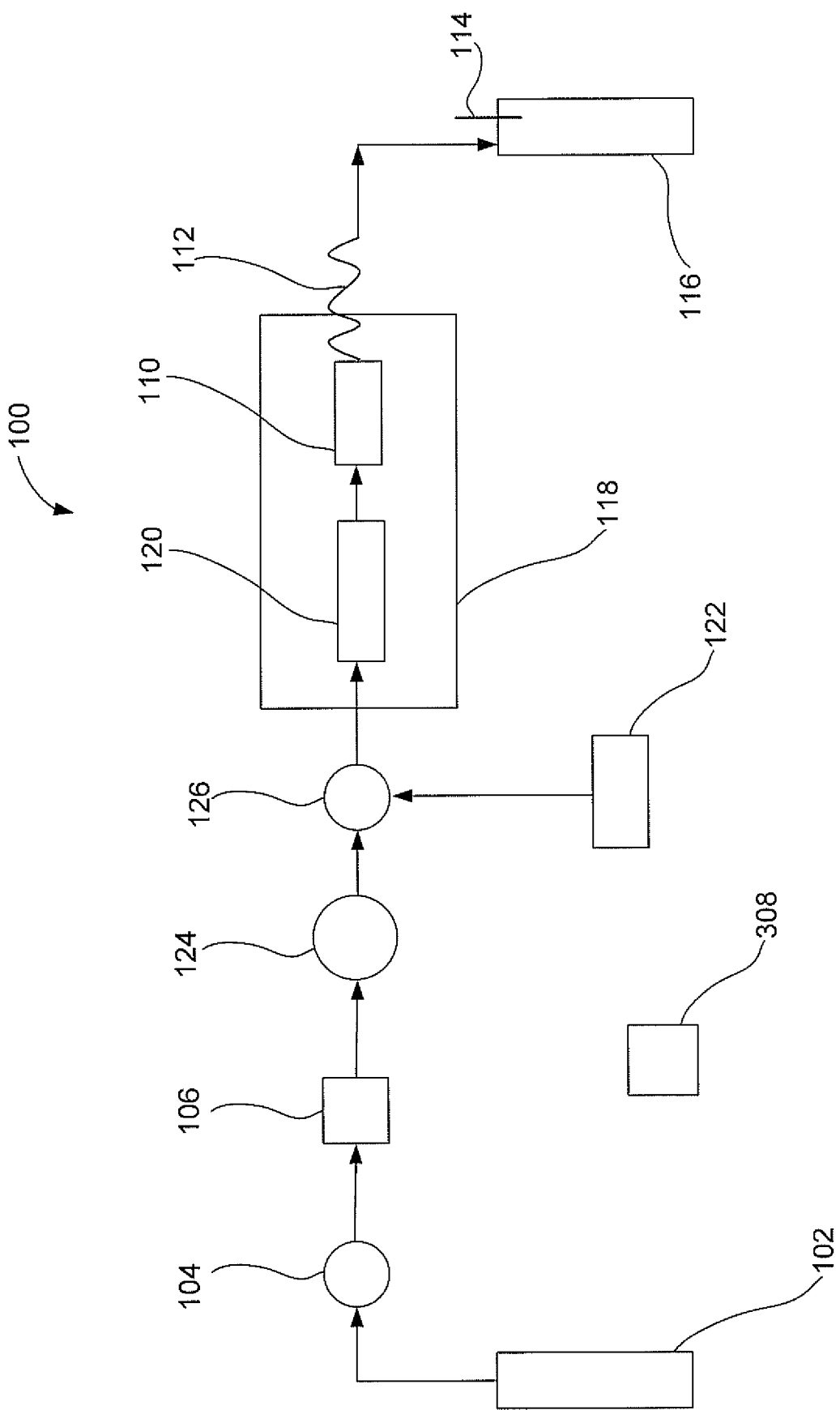
FIG. 1 illustrates a first embodiment of an apparatus to extract an analyte from a sample with gas assistance.

FIG. 1 illustrates a first embodiment of a solid liquid extraction apparatus 100 to extract an analyte from a sample with gas assistance. Apparatus 100 may include a compressed gas source 102, a gas valve 104, a check valve 106, a six port valve 124, a fluid junction 126, a liquid solvent pump 122, a solvent equilibration chamber 120, a sample container 110, a restriction tube 112, a collection bottle 116, and a microprocessor 308. Compressed gas source 102 can be fluidically connected to supply a gas to sample container 110. Liquid solvent pump 122 can be fluidically connected to supply a liquid solvent to sample container 110. Sample container 110 can be configured to contain the solid sample. Sample container 110 can be fluidically connected to collection bottle 116 to allow the transfer of the liquid solvent containing the dissolved analyte and the gas.

An output of compressed gas source 102 can also be fluidically connected to gas valve 104, check valve 106, six port valve 124, fluid junction 126, and solvent equilibration chamber 120. Compressed gas source 102 can be configured to supply a gas at a superatmospheric pressure. The term superatmospheric pressure refers to a pressure that is greater than an ambient pressure surrounding an external portion of apparatus 100. A typical ambient pressure, in which the extraction apparatus may be used, may range from about 13.7 PSI to about 15.2 PSI. In an embodiment, the superatmospheric pressure may be less than about 2000 PSI, and preferably be less than about 100 PSI. It should be noted that a magnitude of the pressures within the solid liquid extraction apparatus denoted herein are stated as a "gauge pressure" and thus are listed relative to an ambient pressure. In an alternative embodiment, compressed gas source 102 may be in the form of a mechanical gas pump coupled to an air reservoir and configured to provide pressurized air.

Gas valve 104 is configured to control the flow rate of the gas from compressed gas source 102. The applied superatmospheric pressure may be measured at gas valve 104. Gas check valve 106 is configured to prevent a backflow of liquid solvent into compressed gas source 102. Six port valve 124 is configured to either allow the flow of gas to sample container 110 or to stop the flow of gas. Under certain circumstances, where only liquid solvent flow is directed to sample container 110, six port valve 124 can stop the flow of gas to sample container 110.

An output of liquid solvent pump 122 can be fluidically connected to fluid junction 126. Liquid solvent pump 122 can be configured to transport the liquid solvent at a pressure that is less than 100 PSI. Although high pressure is not needed, liquid solvent pump 122 may be in the form of a high pressure liquid chromatography (HPLC) pump. Alternatively, liquid solvent pump 122 may be in the form of a compressed gas source coupled to a liquid solvent reservoir. The source of compressed gas may come from compressed gas source 102 where it is used to provide the gas for extraction and also to pump the liquid solvent from the liquid solvent reservoir. Instead of using only one compressed gas source, it is also possible to use two compressed gas sources where a second compressed gas cylinder can be used to pump the liquid solvent from the liquid solvent reservoir. Examples of liquid solvents suitable for use in the extraction method described herein may be methanol, ethanol, isopropanol, hexane, dichloromethane, and combinations thereof. Liquid solvent(s) may be selected that have a polarity similar to the analyte of interest.

Fluid junction 126 can be configured to mix the gas from compressed gas source 102 and the liquid solvent from the liquid solvent pump 122. Fluid junction 126 can include a first inlet, a second inlet, and an outlet, where the first inlet and second inlet are both fluidically connected to the outlet. The first inlet can be in fluidic communication with compressed gas source 102. The second inlet can be in fluidic communication with liquid solvent pump 122. The outlet can be configured to flow a mixture of the gas and the liquid solvent at the same time into an inlet of sample container 110. Fluid junction 126 may be in the form of a Tee junction.

Liquid solvent may be heated to extract the analyte from the solid sample in a variety of ways. Solvent equilibration chamber 120 can be configured to heat the liquid solvent to an elevated temperature before the liquid solvent is added to the sample container 110. A temperature controller 118 can be configured to heat solvent equilibration chamber 120 and/or sample container 110 to a value greater than ambient. Temperature controller 118 can be referred to as a heating source and may be in the form of a microwave device, an electrically resistive device, an infrared device, a convection heater, or a combination thereof. In an embodiment as illustrated in FIG. 1, temperature controller 118 can be used to control the temperature of the liquid solvent at solvent equilibration chamber 120 and also at sample container 110. However, in an alternative embodiment, temperature controller 118 can be used to control the temperature of solvent equilibration chamber 120 and not for sample container 110. In such a case, sample container 110 may include an insulated jacket to prevent significant cooling of the heated liquid solvent. In yet another alternative embodiment, temperature controller 118, can be used to control the temperature of sample container 110 and not for solvent equilibration chamber 120. The heating of sample container 110 can, in turn, heat the liquid solvent for the extraction.

An output of sample container 110 can be fluidically connected to a restriction tube 112. Restriction tube 112 can have a relatively small inner bore diameter to generate a backpressure. In an embodiment, restriction tube 112 can be configured to generate a backpressure of about 10 PSI. It is noted that although pressures are typically measured at gas valve 104, the pressure within sample container 110 will be approximately the same as the applied superatmospheric pressure as measured at gas valve 104. Under certain circumstances, the pressure within sample container 110 may be slightly less than the applied superatmospheric pressure due to pressure drops at various locations, but such a decrease will be insignificant. Restriction tube 112 can generate sufficient backpressure to ensure that the solvent remains in a liquid state at the extraction temperature. If restriction tube 112 is not fluidically connected to sample container 110, then the liquid solvent can evaporate more significantly, and as a result, cause a reduction in the extraction efficiency. After liquid solvent containing dissolved analyte flows through restriction tube 112, it can be transferred to a collection bottle 116. Collection bottle 116 may include a vent 114 so that gas can egress.

Microprocessor 308 can be used to control the operation of apparatus 100. Microprocessor 308 may either be integrated into apparatus 100 or be part of a personal computer that communicates with apparatus 100. Microprocessor 308 may be configured to communicate with one or more components of apparatus 100 such as gas valve 104, a check valve 106, six port valve 124, liquid solvent pump 122, and temperature controller 118. For example, microprocessor 308 can control the flow rate, pressure, temperature, and duration of the gas and liquid solvent flow. In an embodiment, microprocessor 308 can control six port valve 124 to stop the flow of gas so that only liquid solvent flows to sample container 110 as a control experiment. In addition, microprocessor 308 can turn off liquid solvent pump 122 to allow only gas to flow when purging sample container 110.

Figure 2:
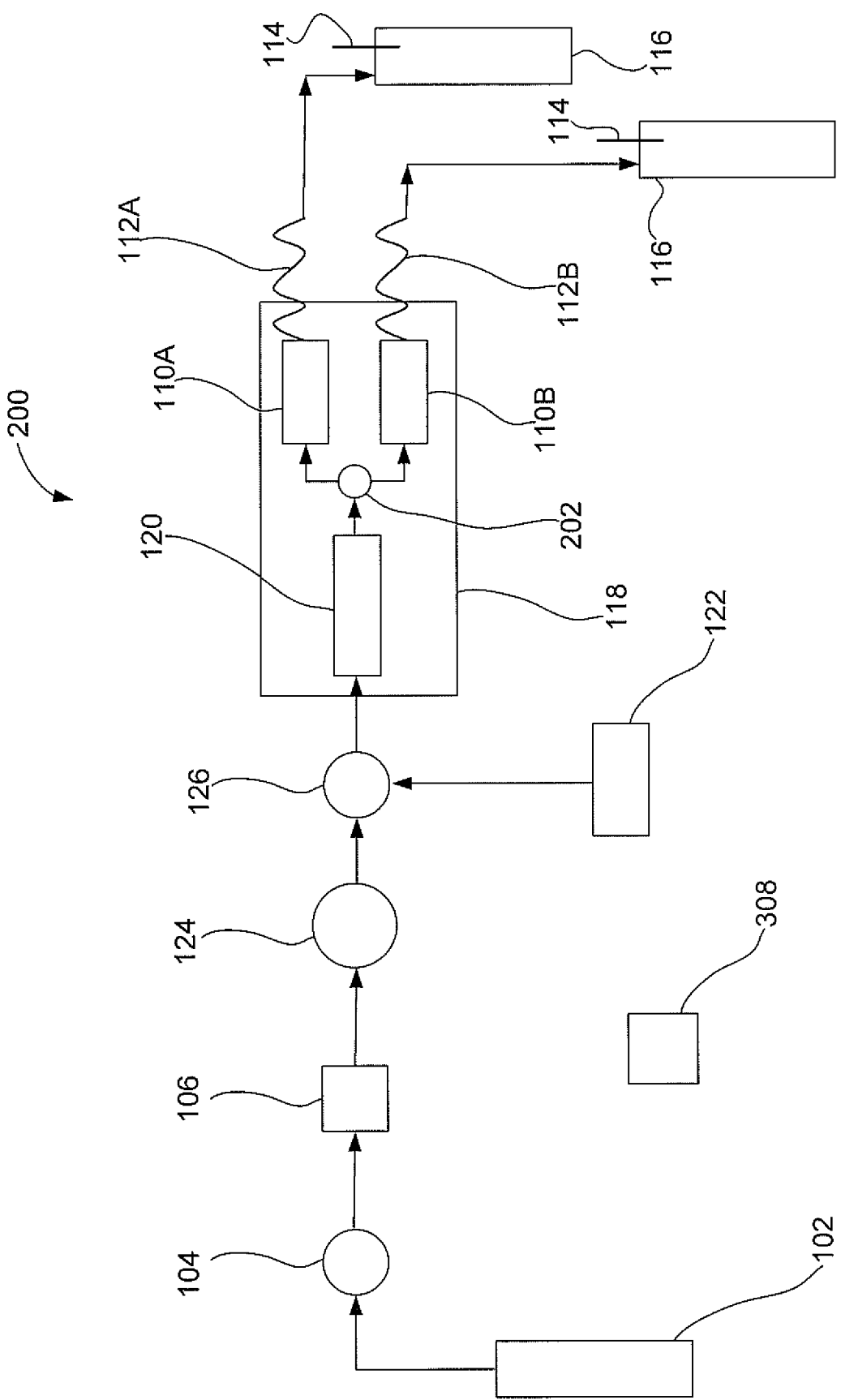
FIG. 2 illustrates a second embodiment of an apparatus that uses a parallel extraction mode to extract an analyte from two samples with gas assistance.

FIG. 2 illustrates a second embodiment of an apparatus 200 that uses a parallel extraction mode to extract an analyte from two solid samples with gas assistance. Apparatus 200 is similar to apparatus 100 except that apparatus 200 includes two sample containers 110A and 110B, two restriction tubes 112A and 112B; and two collection bottles 116A and 116B. Apparatus 200 may also includes a second fluid junction 202 that is fluidically connected to solvent equilibration chamber 120 and sample containers 110A and 110B. Second fluid junction 202 may be in the form of a Tee valve. In an embodiment, first sample container 110A and second sample container 110E may both be fluidically connected to the outlet of the second fluid junction 202. Apparatus 200 is configured to evenly split the flow of the liquid solvent mixture into sample containers 110A and 110B. The gas and liquid solvent mixture should input into both sample containers at the same time. It should be noted that the description of two sample containers for use with apparatus 200 is exemplary and should not be construed as being limited to only two sample containers. The parallel extraction mode as described herein can be applied to two or more sample containers so that multiple solid sample extractions can be performed at the same time.

Figure 3:
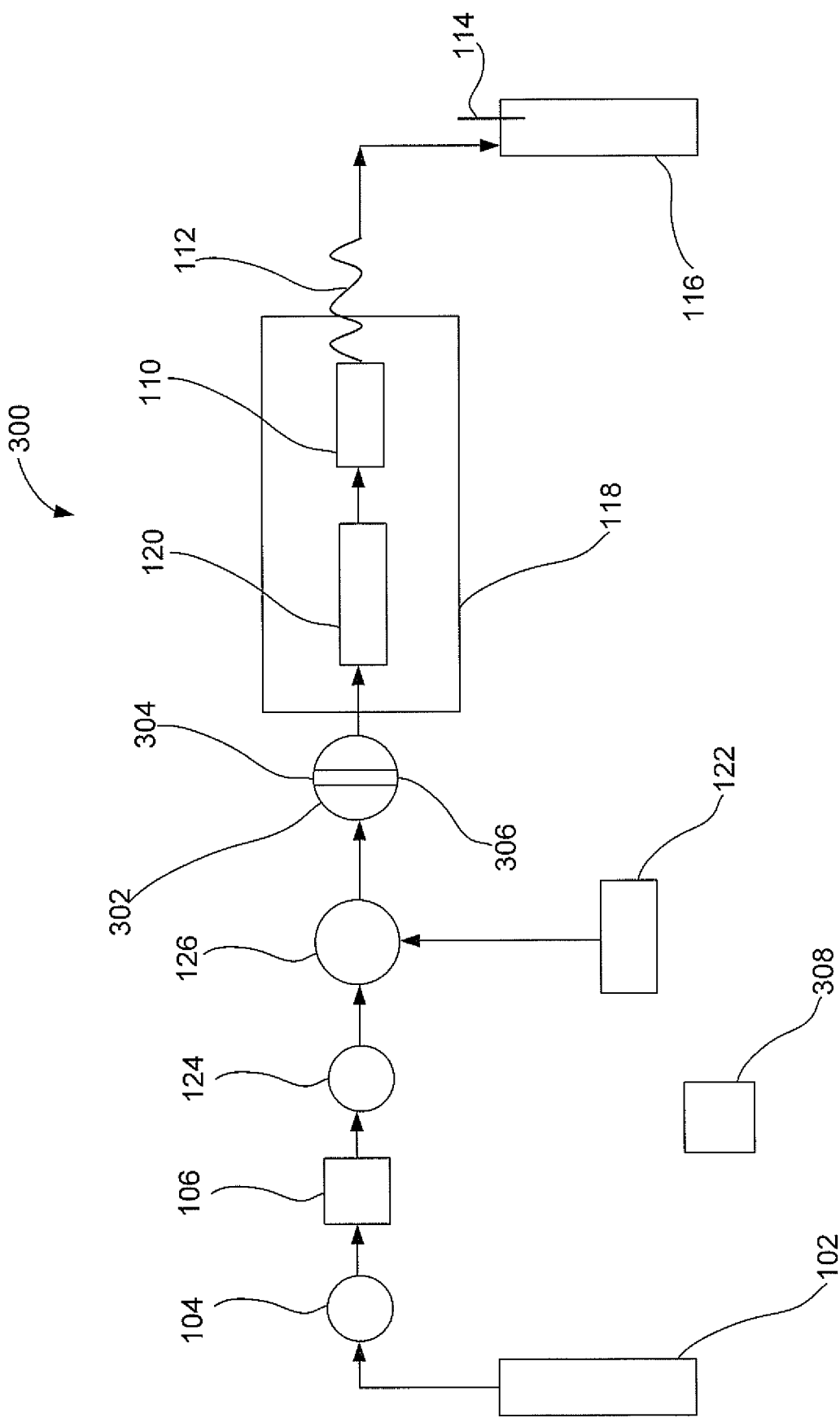
FIG. 3 illustrates a third embodiment of an apparatus that uses an alternating segmented flow of a gas and then a liquid solvent to extract an analyte from a sample.

FIG. 3 illustrates a third embodiment of an apparatus that uses an alternating segmented flow of a gas and then a liquid solvent to extract an analyte from a solid sample. Apparatus 300 is configured to alternate as a function of time a segmented flow of either a gas or a liquid solvent flow to sample container 110. Apparatus 300 is similar to apparatus 100 except that apparatus 300 includes a six port valve 302. Six port valve 302 can include an inlet 304 and an outlet 306. Six port valve 302 can be configured to allow either a gas flow or a liquid solvent flow in an alternating manner.

In an embodiment, six port valve 302 may include a first position and a second position. The first position can direct the liquid solvent from liquid solvent pump 122 into sample container 110. The second position can direct the gas from compressed gas source 102 into sample container 110 to establish a superatmospheric pressure P. Six port valve 302 can be coupled to microprocessor 308 to alternate between the first position over a first time period for liquid solvent flow and the second position over a second time period for gas flow. A ratio of the first time period divided by the second time period may include a value less than about 15. A result of having the ratio less than 15 is that the total volume of liquid solvent used in the extraction is relatively low.

In an alternative embodiment, microprocessor 308 may be configured to turn on and off the power to liquid solvent pump 122 to control part of the alternating segmented flow. Microprocessor 308 may be configured to turn on and off the gas flow by controlling one of the valves 104, 124, and 302.

Figure 4:
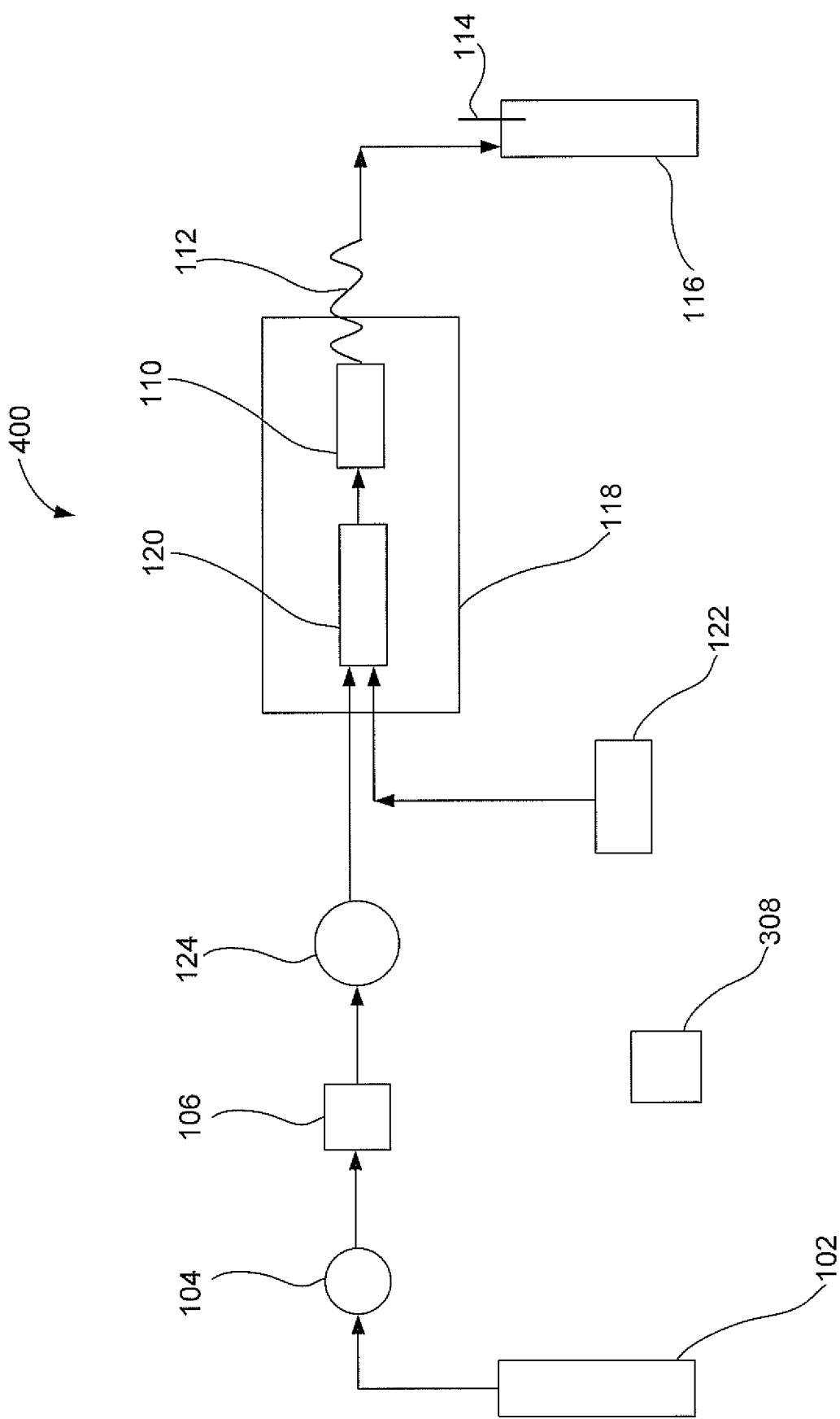
FIG. 4 illustrates a fourth embodiment of an apparatus to extract an analyte from a sample with gas assistance that is an alternative to the first embodiment.

FIG. 4 illustrates a fourth embodiment of a solid liquid extraction apparatus 400 to extract an analyte from a sample with gas assistance. Apparatus 400 is similar to apparatus 100 except that apparatus 400 does not include a fluid junction 126. Instead, apparatus 400 includes a solvent equilibration chamber 120 with two inlets. As illustrated in FIG. 4, solvent equilibration chamber 120 includes a first inlet configured to receive the liquid solvent and a second inlet configured to receive the gas. Solvent equilibration chamber 120 of apparatus 400 can perform a similar mixing function as fluid junction 126 of apparatus 100. For situations where solvent equilibration chamber 120 is not required, sample container 110 can include a first inlet configured to receive the liquid solvent and a second inlet configured to receive the gas (not shown). Thus, embodiments of the solid liquid extraction apparatus described herein may include a means for providing a mixture of the liquid solvent and gas to the sample container. The means for providing a mixture of the liquid solvent and gas to the sample container may include the use of fluid junction 126 of FIG. 1, dual inlets on solvent equilibration chamber 120 of FIG. 4, or dual inlets on the sample container.

Now that embodiments of the solid liquid extraction apparatus have been described, the following will describe methods of extracting the analyte from the solid sample. The method includes adding a solid sample to sample container 110. Typically, the solid sample is weighed before putting it into sample container 110. A mixture of a liquid solvent and a gas can be added to the sample container. The addition of gas can be controlled to establish a superatmospheric pressure P within sample container 110. The liquid solvent can be heated to an elevated temperature T that is below the boiling temperature of the liquid solvent. Either the pressure P or the temperature T should be maintained below the critical point of the gas. The analyte from the solid sample can then dissolve into the liquid solvent. Next, at least a portion of the liquid solvent can be removed from sample container 110.

The portion of liquid solvent containing the dissolved analyte can be analyzed with an analytical instrument to determine the amount of analyte present in the solid sample. For example, where a separation of the analyte from other chemicals present in the liquid solvent is needed, liquid or gas chromatography may be performed. A detector may be used alone or in combination with the separation process. Exemplary detectors may be a mass spectrometer, ultraviolet-visible spectrometer, a fluorescence spectrometer, a flame ionization detector, a charged aerosol detector, an electrochemical detector, a conductometric detector, a charge detector, or a combination thereof. Details regarding the charged aerosol detector can be found in U.S. Pat. Nos. 6,544,484; and 6,568,245, which are hereby fully incorporated by reference herein. Details regarding the charge detector that is based on a charged barrier and two electrodes can be found in US Pre-Grant Publication No. 20090218238, which is hereby fully incorporated by reference herein.

In an embodiment, the gas is added so that the pressure in the sample container is less than about 2000 PSI, and is preferably less than about 100 PSI. The liquid solvent may be heated to an elevated temperature that ranges from about 30° C. to about 300° C. The elevated temperature is a temperature value greater than an ambient temperature. The ambient temperature may refer to an environmental temperature that is surrounding an external portion of apparatus 100 when the extraction process is performed. Where apparatus 100 is used in an outside environmental setting, the ambient temperature may range from about 5° C. to about 45° C. In an embodiment, the liquid solvent may be heated to a temperature greater than ambient before adding the gas and liquid solvent mixture to sample container 110. In another embodiment, the mixture of gas and liquid solvent may be heated once it is added to sample container 110.

Note that the added gas should be selected so that it will not transition to a supercritical fluid or a liquid state over the above described pressure and temperature ranges. In an embodiment, the selected gas is a substance that remains in a distinct gas phase at the operating conditions of the extraction process conditions described herein, i.e., the selected gas does not condense into the liquid phase, and is maintained at a temperature and a pressure below its critical point such that it does not take the form a supercritical fluid. As is known in the art, the critical point refers to a characteristic temperature and the pressure above which distinct liquid and gas phases do not exist. It should be noted that the critical temperature and the critical pressure are intrinsic properties of a particular gas.

In another embodiment, the gas may be an inert gas such as helium, neon, argon, or combinations thereof. Other exemplary gases suitable for use in the embodiments described herein may also include nitrogen, carbon dioxide, air, hydrogen, oxygen, or combinations thereof. The added gas causes the pressure to increase in the sample container and increases the boiling point of the liquid solvent. When performing an extraction, a particular combination of pressure and temperature can be selected so that the liquid solvent does not boil. The elevated temperature facilitates the dissolution of analyte into the liquid solvent from the solid sample. The pressure can prevent the liquid solvent from boiling, and thus, maintains and enhances the solvating ability of the liquid solvent. When the liquid solvent boils, this can decrease the amount of liquid solvent available to dissolve the analyte.

In an embodiment, the adding of the mixture of gas and liquid may be an essentially continuous flow through sample container 110. The mixture of the gas and the liquid solvent can be created by adding the gas at a first flow rate and by adding the liquid solvent at a second flow rate. The ratio of the first flow rate to the second flow rate may range from about 0.01 to about 5000, and preferably range from about 1.1 to about 5000. It should be noted that the pressure of the gas is based on the input at valve 104.

Applicants believe that the addition of gas can increase the diffusion of the liquid solvent to and from the solid sample, which in turn, provides assistance in the extraction process. The diffusion of the gas phase can be several orders higher than the liquid solvent phase. Thus, the gas addition increases the overall mass transfer properties of the liquid solvent even though the gas by itself does not dissolve the analyte.

EXAMPLE 1

The following will describe an example of a solid liquid extraction using gas assistance where the analyte was a lipid. Various solid food samples were analyzed, which were infant formula, corn chips, parmesan cheese, and cake mix. All reagents used in this work were analytical grade unless specified otherwise. Hexane, ACS grade (Sigma-Aldrich, St. Louis, Mo., USA), dichloromethane, ACS grade (Sigma-Aldrich, St. Louis, Mo., USA), methanol HPLC grade (Honeywell Burdick and Jackson, Muskegon, Mich.), and isopropanol (General Chemicals, Parsippany, N.J.) were used as extraction solvents. Similac® Advance® infant formula was from Abbot Laboratories (Columbus, Ohio). Fritos® corn chips were from Frito-Lay (Plano, Tex.). The parmesan cheese was from Kraft Foods (Northfield, Ill.). Pillsbury® cake mix was from Pillsbury, Minn. The diatomaceous earth absorbent (ASE Prep DE) was from Thermo Scientific Dionex (Sunnyvale, Calif.).

Referring back to FIG. 1, liquid solvent pump 122 was a high pressure liquid chromatography (HPLC) pump from Thermo Scientific Dionex (part number P680A DGP-6, Sunnyvale, Calif.). Compressed gas source 102 was a nitrogen gas cylinder from Airgas-NCN (Sacramento, Calif.) with an adjustable pressure regulator valve 104. The nitrogen flow was measured with a Mass Trak flow meter (Sierra Instruments, Monterey, Calif., Model 810C-DR-13). Check valve 106 was obtained from Upchurch Scientific/IDEX Corp (CV-3001 and U-469, check valve inline cartridge and cartridge holder, Oak Harbor, Wash.).

A 6 port valve 124 (Rheodyne, model 1505, Upchurch Scientific/IDEX Corp, Oak Harbor, Wash.) was connected to the gas stream by using Green PEEK tubing (0.03 inch inner diameter). The purpose of the 6 port valve was to route the gas for the gas assisted solvent extraction and for the nitrogen purge. In one position the gas flowed for either purging purposes or for mixing with the flow of liquid solvent. In a second position, the gas flow was blocked where the extraction proceeded without gas assistance.

Temperature controller 118 was a column temperature controller from Pickering Laboratories (CHX700, Mountain View, Calif.). Solvent equilibration chamber 120 was a stainless steel solvent column (4.6×250 mm, volume of 4.15 mL, Isolation Technologies, IDEX Health and Science, Middleboro, Mass.). Sample container 110 was a stainless steel sample column (7.8×75 mm, volume of 3.58 mL, Isolation Technologies, IDEX Health and Science, Middleboro, Mass.). As illustrated in FIG. 1, solvent equilibration chamber 120 and sample container 110 were both incorporated into temperature controller 118. Solvent equilibration chamber 120 and sample container 110 were connected using stainless steel tubing (0.03 inch I.D.) inside the column holder.

Restriction tube 112 was a stainless steel tube with a 0.01 inch inner diameter×3.93 inch length. Red PEEK™ tubing (0.005 inch inner diameter×3.0 inch length) was used in between an outlet of sample container 110 and collection bottle 116. The generated backpressure caused by the nitrogen gas was approximately 10 PSI at a 0.6 mL/min liquid solvent flow. Collection bottle 116 was obtained from Thermo Scientific Dionex (250 mL, clear collection bottle, P/N 056284).

About 0.7 to 1.0 gram of ground ASE™ Prep DE was placed into a weighing pan. Next, an amount of infant baby formula (usually 0.7-1.0 grams) was placed into the same weighing pan and measured to the nearest 0.0001 grams. The weight ratio of DE to solid sample was typically at a ratio of about 1:1 or higher. The DE and the solid food sample were both placed into a mortar and ground thoroughly by a pestle. A sample container included a stainless steel column (7.8 mm×75 mm, volume of 3.58 mL, Isolation Technologies, IDEX Health and Science, Middleboro, Mass.). The sample container was assembled by first placing a bottom frit and end cap, followed by the addition of the ground DE and solid food sample to the inside portion of the container. Next, a top end cap with a frit was assembled to complete the assembly of sample container 110.

Temperature controller 118 was thermally equilibrated to a 100° C. Sample container 110 containing the solid sample was loaded into apparatus 100. A liquid solvent of hexane, dichloromethane, and methanol (volume ratio of 5:2:1) was flowed through sample container 110 at a flow rate of about 0.5 mL/min for about 30 minutes. Compressed gas source 102 was turned on to output nitrogen gas at a flow rate ranging from about 0.17 to 0.20 standard liters per minute (SLPM) to establish a pressure ranging from about 30 PSI to about 60 PSI. The gas was flowed through sample container 110 at the same time as the liquid solvent. The adding of the mixture of the gas and liquid solvent was an essentially continuous flow through the sample container. After the liquid solvent pump was stopped, the gas flow was allowed to continue for an additional four minutes. Next, sample container 110 was allowed to depressurize for at least a two minute period. Sample container 110 was then disconnected so that another solid sample could be loaded and then extracted. The liquid solvent containing the dissolved lipids was collected in 250 mL collection bottles. The amount of lipids was then determined gravimetrically and compared to the amount listed on the packaging label. Details regarding the gravimetric analysis of lipids in an extracted liquid solvent can be found in the Product Manual for ASE Prep CR H+ form (Thermo Scientific Dionex) and in US Pre-Grant Publication No.'s 2009/0221079A1 and 2012/0028368A1, which are hereby fully incorporated by reference herein. Table 1 shows the results of a solid liquid extraction of lipids from the infant baby formula where the lipid recovery percentage and the volume of collected solvent was a function of the nitrogen gas pressure.

TABLE 1

| Liquid Solvent Flow Rate, mL/min | $N_2$ Gas Pressure, PSI | Lipid Recovery, % | Solvent Collected Post Extraction, mL |
| --- | --- | --- | --- |
| 0.50 | 0 | 88.2 | 13 |
| 0.50 | 30 | 86.0 | 13 |
| 0.50 | 40 | 92.9 | 13 |
| 0.50 | 45 | 93.8 | 12 |
| 0.50 | 50 | 94.1 | 11 |
| 0.50 | 55 | 94.8 | 11 |
| 0.50 | 60 | 95.8 | 10 |
| 0.50 | 70 | 96.5 | 9 |
| 0.50 | 90 | 96.5 | 7 |

The nitrogen gas pressure was found to have an effect on the lipid recovery percentage where increasing the gas pressure improved the recovery percentage. In particular, a zero PSI nitrogen gas pressure provided a lipid recovery of 88.2% as opposed to a lipid recovery of 96.5% at a 70 PSI nitrogen gas pressure. It should be noted that zero PSI nitrogen gas refers to the condition where no nitrogen gas was added to the sample container. For this situation where nitrogen gas is not added, the sample container can have a pressure higher than ambient due to pressure induced by the heated solvent. The results in Table 1 indicate that substantially all of the lipid analyte is extracted when using gas assisted extraction at about 60 PSI nitrogen or greater. In addition to the recovery percentage being improved when the nitrogen pressure was increased, the collected volume of liquid solvent was decreased. At zero PSI nitrogen gas pressure, the collected liquid solvent volume was 13 mL as opposed to the smaller volume of 9 mL at 70 PSI. The evaporation of the liquid solvent was enhanced due to the gas flow. Thus, not only is the recovery percentage improved at higher pressures, but the analyte is more concentrated in the liquid solvent without requiring an additional processing step. This can be an advantage where liquid solvent needs to be removed before the analytical measurement.

EXAMPLE 2

The following experiment was performed to determine the effect of solvent flow rate on the solid liquid extraction. Example 2 was performed in a manner similar to Example 1 using infant baby formula as the solid sample with a liquid solvent flow duration of 30 minutes at 100° C. In this Example, the extraction process was also evaluated where the gas pressure applied to sample container 110 was either zero or 60 PSI of nitrogen. Table 2 shows the lipid recovery percentage and the volume of liquid solvent collected where the liquid solvent flow rate was varied from 0.25 mL/min to 1.5 mL/min.

TABLE 2

| Liquid Solvent Flow Rate, mL/min | 0 PSI Nitrogen Gas | | 60 PSI Nitrogen Gas | |
|---|---|---|---|---|
| | Lipid Recovery, % | Solvent Collected Post Extraction, mL | Lipid Recovery, % | Solvent Collected Post Extraction, mL |
| 0.25 | 23.1 | 6 | 38.0 | 2 |
| 0.40 | 65.6 | 10 | 95.8 | 8 |
| 0.50 | 88.2 | 13 | 95.1 | 10 |
| 0.60 | 88.9 | 16 | 100.6 | 14 |
| 0.75 | 93.45 | 20 | 100.3 | 18 |
| 1.0 | 97 | 28 | 102.2 | 27 |
| 1.5 | 102.5 | 42 | NA | NA |

At zero PSI nitrogen, the recovery percentage improved with the increasing flow rate of the liquid solvent. Near 100% recovery was obtained for a flow rate of about 1.5 mL/min at zero PSI nitrogen, which resulted in a total solvent usage (calculated) of about 45 mL (30 minutes×1.5 mL/min). The observed liquid solvent volume at zero PSI nitrogen was about 42 mL because there was some evaporation. When the same solid sample was extracted at 60 PSI nitrogen, near 100% recovery was achieved at a flow rate of 0.6 ml/min which resulted in a net solvent usage (calculated) of about 18 ml (30 minutes×0.6 mL/min). At 60 PSI nitrogen, the observed liquid solvent volume was about 14 ml. Thus, by performing the extractions with a combination of a liquid solvent and a gas stream, the liquid solvent usage diminished significantly (by about 60% in the above example, 45 mL to 18 mL). Further, an analyte dissolved in 14 mL of liquid solvent is three-fold more concentrated than a sample dissolved in 42 mL of liquid solvent. The gas assisted mode not only reduces solvent usage, but also improves the sensitivity via concentrating the analyte of interest. In some cases, the solvent evaporation step can be eliminated since the sample in the gas assisted extraction case is already concentrated. Surprisingly, a more efficient extraction process was developed that uses a lower flow rate, and in turn, a smaller volume of liquid solvent, with a combination of a modest temperature (less than 300° C.) and pressure (less than 100 PSI).

EXAMPLE 3

The following experiment was performed to determine the effect of the extraction time on the lipid recovery percentage. Example 3 was performed in a manner similar to Example 1 using infant baby formula as the solid sample with a liquid solvent flow rate of 0.6 mL/min and a temperature of 100° C. In this Example, the extraction process was also evaluated where the gas pressure applied to sample container 110 was either zero or 60 PSI of nitrogen. Table 3 shows the lipid recovery percentage and the volume of liquid solvent collected where the duration of the liquid solvent flow was varied from 10 minutes to 30 minutes.

TABLE 3

| Liquid Solvent Flow Rate, mL/min | Extraction Time, min | 0 PSI Nitrogen Gas | | 60 PSI Nitrogen Gas | |
|---|---|---|---|---|---|
| | | Lipid Recovery, % | Solvent Collected Post Extraction, mL | Lipid Recovery, % | Solvent Collected Post Extraction, mL |
| 0.60 | 10 | 75.0 | 5 | 51.8 | 4 |
| 0.60 | 20 | 81.1 | 11 | 100.4 | 9 |
| 0.60 | 30 | 88.9 | 16 | 100.6 | 14 |

At zero PSI nitrogen, the recovery percentage improved with the increasing duration of the extraction time. However, a 30 minute extraction time at zero PSI nitrogen was not long enough to achieve a near 100% recovery. In contrast, a 20 minute extraction time at 60 PSI nitrogen was sufficient to achieve a near 100% recovery of the lipid. By performing the extractions with a combination of a liquid solvent and a 60 PSI nitrogen gas stream, a near 100% extraction was achieved in a shorter time duration of 20 minutes as opposed to requiring more than 30 minutes at zero PSI nitrogen. Thus, the gas assisted mode not only reduces solvent usage and improves the sensitivity via concentrating the analyte of interest, but it also performs the extraction in a faster time frame. In general, more solid samples can be processed with the extraction apparatus when the extraction time is faster.

EXAMPLE 4

The following experiment was performed to determine the effect of the gas alone on the lipid recovery percentage. The purpose of this experiment was to show that gas by itself did not have any solvating power. Example 4 was performed in a manner similar to Example 1 using infant baby formula as the solid sample with a liquid solvent flow rate of either 0 mL/min or 0.6 mL/min at 100° C. The gas pressure applied to sample container 110 was varied from abut zero to about 500 PSI nitrogen. For the condition where the liquid solvent flow rate was zero, about 10 mL of liquid solvent was placed in sample container 110 to aid in the extraction of the lipids. Table 4 shows the lipid recovery percentage and the volume of liquid solvent collected where the liquid solvent flow was either zero or 0.6 mL/min.

TABLE 4

| Liquid Solvent Flow Rate, mL/min | N$_2$ Gas Pressure, PSI | Lipid Recovery, % | Solvent Collected Post Extraction, mL |
|---|---|---|---|
| None | 60 | 0 | — |
| None | 500 | 0 | — |
| 0.6 | 0 | 88.9 | 16 |
| 0.6 | 60 | 100.6 | 14 |
| 0.6 | 500 | 101.3 | 15 |

The above results show that with the gas stream by itself as the extraction or flowing media did not aid in any recovery of lipids. This was highlighted by the fact that no lipids were recovered in the absence of a liquid solvent flow when the added gas was at either 60 PSI or even up to 500 PSI nitrogen. No solvent was collected for the condition where there was no liquid solvent flow because of evaporation. For the situation where the liquid solvent was flowed at 0.6 mL/min, it should be noted that increasing the gas pressure from 60 PSI nitrogen to 500 PSI nitrogen was not needed for improving the lipid recovery percentage.

EXAMPLE 5

The following experiment was performed to evaluate the possible effect of the type of gas used in the extraction. Example 5 was performed in a manner similar to Example 1 using infant baby formula as the solid sample with either nitrogen, air, or helium as a type of gas for the compressed gas source. The added gas pressure and liquid solvent temperature were at 60 PSI and 100° C., respectively. The liquid solvent flow rate was 0.6 mL/min for a duration of 30 minutes. Table 5 shows the effect of gas type on lipid recovery percentage and volume of collected liquid solvent.

TABLE 5

| Liquid Solvent Flow Rate, mL/min | Gas Type and Pressure in PSI | Lipid Recovery, % | Solvent Collected Post Extraction, mL |
|---|---|---|---|
| 0.6 | N$_2$, 60 | 100.6 | 14 |
| 0.6 | Air, 60 | 99.2 | 13 |
| 0.6 | Helium, 60 | 100.1 | 14 |

The above results indicated that the type of gas used in the extraction had minimal to no impact on the recovery percentage. All of the three gas streams showed similar recoveries and provided the same benefit of relatively low solvent usage.

EXAMPLE 6

The following experiment was performed to determine the feasibility of a parallel extraction mode. Example 6 was performed using apparatus 200 with infant baby formula as the solid sample with a liquid solvent flow rate of 1.2 mL/min for a duration of 30 minutes at 100° C. Hexane:dichloromethane:methanol with a volume ratio of 5:2:1 was used as the liquid solvent. The nitrogen pressure that was applied was either zero PSI or 60 PSI. Where nitrogen gas was used, the gas and liquid solvent were flowed at the same time. Fluid junction 126 was used to split the mixture of gas and liquid solvent. In contrast to Example 1, this experiment extracted analyte from two separate sample containers 110A and 110B at the same time. Table 6 shows the lipid recovery percentage and the volume of liquid solvent collected where the nitrogen gas flow was tested at zero and 60 PSI. Note that Sample-1 corresponded to the extraction of first sample container 110A and Sample-2 corresponded to the extraction of second sample container 110B, which were extracted at the same time increasing sample throughput.

TABLE 6

| | 0 PSI Nitrogen Gas | | 60 PSI Nitrogen Gas | |
|---|---|---|---|---|
| Parallel Extraction | Lipid Recovery, % | Solvent Collected Post Extraction, mL | Lipid Recovery, % | Solvent Collected Post Extraction, mL |
| Sample-1 | 92.1 | 14 | 100.7 | 13 |
| Sample-2 | 92.2 | 19 | 100.6 | 15 |

The results from the above table indicated a higher lipid recovery percentage at 60 PSI nitrogen gas assisted mode of operation as compared to the zero PSI extraction. One of the challenges encountered with a parallel extraction mode is splitting the volume of the liquid solvent in a precise manner so that each sample container receives an equal volume of liquid solvent. For instance, sample container 110A and 110B should each receive 18 mL of liquid solvent from a total volume of 36 mL of liquid solvent that was pumped. Surprisingly, from the volume of the solvent collected, the gas assisted mode at 60 PSI was found to be more effective in splitting the liquid solvent into equal portions than the mode at zero PSI nitrogen gas. For the zero PSI extraction, the volume difference in liquid solvent delivered to the two sample containers was 5 mL (19 mL-14 mL) as compared to the volume difference at 60 PSI, which was 2 mL (15 mL-13 mL). This data shows that it was easier to split the gas-liquid solvent stream rather than the liquid solvent stream by itself with no added nitrogen gas. It should be noted that at zero PSI, the liquid solvent pump by itself is responsible for transporting the liquid solvent to the sample containers and does not split the liquid solvent flow evenly past the fluid junction. Applicants believe that the improved liquid solvent splitting using gas assistance was due to the high diffusion of the gas medium that enables facile splitting of the solvent streams. One of the benefits of the gas assisted parallel extraction mode is faster throughput since multiple extractions can be completed at the same time.

EXAMPLE 7

The following experiment was performed to assess the liquid solvent splitting capabilities with apparatus 200. Example 7 was performed in a manner similar to Example 6 except that the collected liquid solvents collected were weighed to provide more accurate volume estimations. Table 7 shows the volume of liquid solvent collected in a parallel extraction mode where the nitrogen gas flow was tested at zero and 60 PSI.

TABLE 7

| 0 PSI Nitrogen Gas | | 60 PSI Nitrogen Gas | |
|---|---|---|---|
| Channel-1, Solvent Collected Post Extraction, mL | Channel-2, Solvent Collected Post Extraction, mL | Channel-1, Solvent Collected Post Extraction, mL | Channel-2, Solvent Collected Post Extraction, mL |
| 14.39 | 18.18 | 15.44 | 15.54 |

The results showed that the Channel-1 to Channel-2 split ratio from the liquid solvent stream splitting at 60 PSI nitrogen gas was more uniform compared to the liquid solvent stream splitting at zero PSI nitrogen gas. Note that Channel-1 and Channel-2 of Example 7 would fluidically connect to a first sample container and a second sample container, respectively. Because liquid solvent streams are hard to split in equal portions without gas assistance, a solution would be to have independent pumps to provide a controlled liquid solvent flow stream for each channel. However, the use of multiple liquid solvent pumps will cause a substantial increase in the expense of the apparatus. With the gas assisted solvent streams described herein, there is no need for additional pumps and the mixture of gas and liquid solvent streams are easily split and provide more even flow split ratios.

EXAMPLE 8

The following experiment was performed to evaluate the possible effect of an alternating segmented flow of the gas and the liquid solvent on the recovery percentage. In this setup, a bolus of liquid solvent was added followed by a bolus of gas or vice-versa in place of continuously adding the liquid solvent and the gas. FIG. 3 illustrates a simplified schematic of the experimental set-up for the gas assisted extraction in the segmented flow mode. The 6 port valve 302 was fitted with a sample loop of 0.20 mL.

There were two types of modes to input the liquid solvent or the nitrogen gas. The two modes are referred to as the load mode and the inject mode. In the load mode, nitrogen gas flowed through nitrogen gas inlet 304 and filled the loop and exited through outlet 306 and liquid solvent was pumped to sample container 110 at 0.60 mL/min for 100 seconds. In the inject mode, a bolus of nitrogen was injected into sample container 110 for about 20 seconds and the liquid solvent flowed through the loop for 20 seconds. The two modes switch back and forth for the duration of the 30 minute extraction process. In terms of volume, a 1 mL bolus of liquid solvent was injected into sample container 110 in the load mode and a 0.2 mL bolus of nitrogen gas at 60 PSI was injected into sample container 110 in the inject mode. After the 30 minute extraction process, nitrogen gas was applied to purge sample container 110 to remove any remaining liquid solvent. For Example 8, the extraction temperature was 100° C. and the liquid solvent was hexane:dichloromethane:methanol (5:2:1 volume ratio). The solid sample was infant formula and the analyte was lipids. Table 8 shows the lipid recovery percentage and the volume of liquid solvent collected where the gas flow and liquid solvent flow were delivered in an alternating segmented manner.

TABLE 8

| Liquid Solvent | Extraction | Gas Assisted Extraction Using an Alternating Segmented Flow of Gas and Liquid Solvent | |
|---|---|---|---|
| Flow Rate, mL/min | Time, min | Lipid Recovery, % | Solvent Collected Post Extraction, mL |
| 0.60 | 30 | 101.8 | 11 |

The results indicated an excellent lipid recovery percentage using the alternating segmented flow of the gas and the liquid solvent. The presence of both liquid solvent and gas in sample container 110 was sufficient to provide an efficient extraction of analyte even though the liquid solvent and gas were not simultaneously introduced.

EXAMPLE 9

The following experiment was performed to determine the lipid recovery percentage of a different solid sample, which in this case, was corn chips. Example 9 was performed in a manner similar to Example 1 using a liquid solvent flow duration of 30 minutes and a flow rate of 0.60 mL/min. The nitrogen gas pressure applied to sample container 110 was either zero PSI or 60 PSI. However, the liquid solvent was hexane and was heated to 100° C. Table 9 shows the lipid recovery percentage and the volume of liquid solvent collected where the solid sample was corn chips.

TABLE 9

| | 0 PSI Nitrogen Gas | | 60 PSI Nitrogen Gas | |
|---|---|---|---|---|
| Liquid Solvent Flow Rate, mL/min | Lipid Recovery, % | Solvent Collected Post Extraction, mL | Lipid Recovery, % | Solvent Collected Post Extraction, mL |
| 0.60 | 90.0 | 17 | 97.9 | 16 |

The results in Table 9 indicated excellent lipid recovery using the gas assisted extraction as compared to zero PSI nitrogen gas. The combination of the solvent and the gas stream caused the lipid recovery percentage to increase by about 8%.

EXAMPLE 10

The following experiment was performed to determine the lipid recovery percentage of a different solid sample, which in this case, was parmesan cheese. Example 10 was performed in a manner similar to Example 1 where the nitrogen gas pressure applied to sample container 110 was either zero PSI or 60 PSI. However, the liquid solvent flow rate was 0.50 mL/min for a duration of 12 minutes. The liquid solvent was hexane and isopropanol (3:2 volume ratio) and was heated to 100° C. Table 10 shows the lipid recovery percentage and the volume of liquid solvent collected where the solid sample was parmesan cheese.

TABLE 10

| | 0 PSI Nitrogen Gas | | 60 PSI Nitrogen Gas | |
|---|---|---|---|---|
| Liquid Solvent Flow Rate, mL/min | Lipid Recovery, % | Solvent Collected Post Extraction, mL | Lipid Recovery, % | Solvent Collected Post Extraction, mL |
| 0.50 | 96.3 | 5 | 101 | 5 |

The results in Table 10 indicated excellent lipid recovery using the gas assisted extraction as compared to zero PSI nitrogen gas. The combination of the solvent and the gas stream caused the lipid recovery percentage to increase by about 4%.

EXAMPLE 11

The following experiment was performed to determine the lipid recovery percentage of a different solid sample, which in this case, was cake mix. Example 11 was performed in a manner similar to Example 1 where the nitrogen gas pressure applied to sample container 110 was either zero PSI or 60 PSI, and the liquid solvent flow duration was 30 minutes. However, the liquid solvent flow rate was 0.50 mL/min. The liquid solvent was hexane, dichloromethane, and methanol (5:2:1 volume ratio) and was heated to 100° C. Table 11 shows the lipid recovery percentage and the volume of liquid solvent collected where the solid sample was cake mix.

TABLE 11

| Liquid Solvent Flow Rate, mL/min | 0 PSI Nitrogen Gas | | 60 PSI Nitrogen Gas | |
| --- | --- | --- | --- | --- |
| | Lipid Recovery, % | Solvent Collected Post Extraction, mL | Lipid Recovery, % | Solvent Collected Post Extraction, mL |
| 0.50 | 96.6 | 14 | 100 | 11 |

The results in Table 11 indicated excellent lipid recovery using the gas assisted extraction as compared to zero PSI nitrogen gas. The combination of the solvent and the gas stream caused the lipid recovery percentage to increase by about 3%. Moreover, the evaporation of the collected solvent which is a more volatile combination improves the sensitivity via concentrating the analyte of interest in the gas assisted mode.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of extracting an analyte from a sample, the method comprising:
    adding the sample to a sample container;
    in a first mode, adding a liquid solvent into the sample container over a first time period;
    in a second mode, adding a gas into the sample container over a second time period to establish a superatmospheric pressure P within the sample container, in which a ratio of the first time period divided by the second time period comprises a value less than about 15, in which the first mode and the second mode switch back and forth for a time duration for an extraction process for dissolving the analyte;
    heating the liquid solvent to an elevated temperature T, in which T is below the boiling temperature of the liquid solvent at the superatmospheric pressure P, and in which either P or T is maintained below the critical point of the gas, in which the superatmospheric pressure P is not greater than about 100 pounds per square inch relative to an ambient pressure, in which the heating of the liquid solvent is at a temperature T ranging from about 30° C. to about 300° C.;
    dissolving the analyte from the sample into the liquid solvent; and
    after the time duration for dissolving the analyte, applying the gas to purge the sample container to remove at least a portion of the liquid solvent from the sample container.

2. The method of claim 1, in which the analyte does not dissolve into the gas.

3. The method of claim 1, in which the heating of the liquid solvent occurs before the adding of the liquid solvent to the sample container.

4. The method of claim 1, in which the heating of the liquid solvent occurs by heating the sample container.

5. The method of claim 1, in which the alternating segmented flow creates a presence of the liquid solvent and the gas in the sample container.

6. The method of claim 1, in which the gas is added from a compressed gas source.

7. The method of claim 1, in which the adding of the liquid solvent and the adding of the gas forms a mixture of the gas and the liquid solvent, in which the mixture continuously flows through the sample container, in which an output of the sample container is fluidly connected to a restriction tube, the restriction tube is configured to generate a backpressure to keep the liquid solvent in a liquid state.

* * * * *